(12) United States Patent
Parisi et al.

(10) Patent No.: US 11,547,570 B2
(45) Date of Patent: Jan. 10, 2023

(54) KNEE PROSTHESIS SYSTEM AND METHOD

(71) Applicant: Zimmer, Inc., Warsaw, IN (US)

(72) Inventors: Raymond C. Parisi, Wakarusa, IN (US); Abraham P. Habegger, Warsaw, IN (US); Nick Drury, Warsaw, IN (US); Brian D. Earl, South Bend, IN (US); Charles A. Baldridge, Claypool, IN (US); James C. Harris, Warsaw, IN (US); Scott Dykema, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 462 days.

(21) Appl. No.: 16/102,244

(22) Filed: Aug. 13, 2018

(65) Prior Publication Data

US 2020/0046508 A1   Feb. 13, 2020

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2/3886* (2013.01); *A61F 2002/30616* (2013.01)

(58) Field of Classification Search
CPC .................................. A61F 2/38; A61F 2/3859
See application file for complete search history.

(56) References Cited

U.S. PATENT DOCUMENTS

| | | | |
|---|---|---|---|
| 8,690,954 B2 | 4/2014 | Parisi et al. | |
| 8,764,838 B2 | 7/2014 | Parisi et al. | |
| 8,858,643 B2 | 10/2014 | Parisi et al. | |
| 8,932,365 B2 | 1/2015 | Parisi et al. | |
| 9,072,607 B2 | 7/2015 | Parisi et al. | |
| 2009/0125114 A1* | 5/2009 | May | A61F 2/38 623/20.14 |
| 2012/0323336 A1 | 12/2012 | Parisi et al. | |
| 2013/0211531 A1* | 8/2013 | Steines | A61F 2/3859 623/20.35 |
| 2016/0128840 A1* | 5/2016 | Cappelletti | A61F 2/3859 623/20.15 |

\* cited by examiner

*Primary Examiner* — Matthew W Schall
(74) *Attorney, Agent, or Firm* — Schwegman Lundberg & Woessner, P.A.

(57) ABSTRACT

According to one example, a system for a knee arthroplasty that can optionally comprise: a femoral prosthesis having a joint facing surface and an opposing bone facing surface, wherein the femoral prosthesis has one or more attachment elements at or adjacent the bone facing surface; and one or more features selectively attachable with the femoral prosthesis via the one or more attachment elements, wherein the one or more features comprise one of a box, a stem, or a combination of the box and the stem.

22 Claims, 14 Drawing Sheets

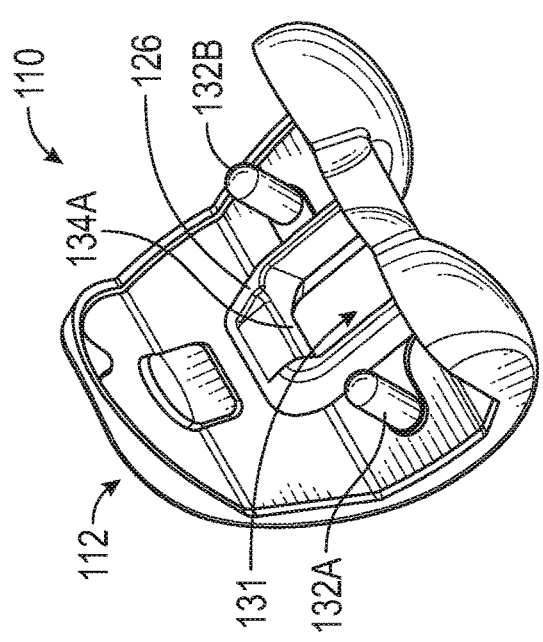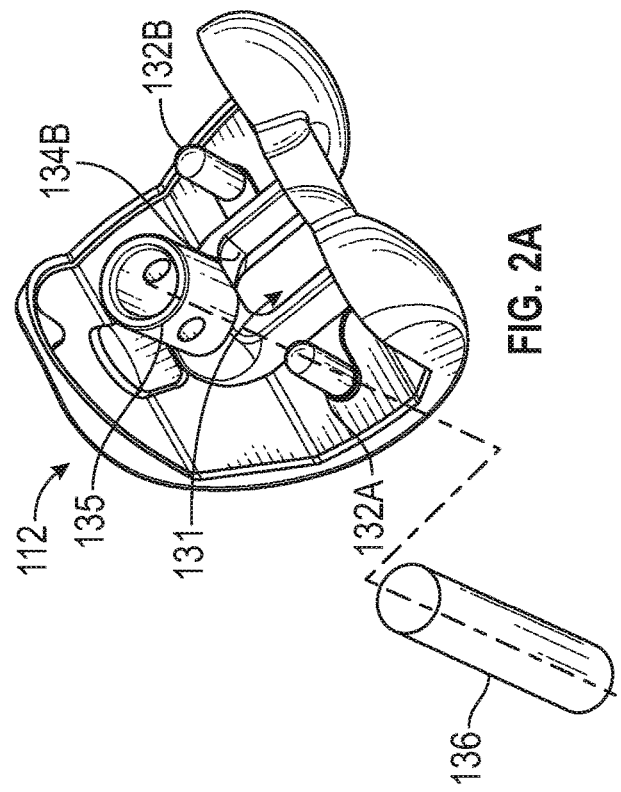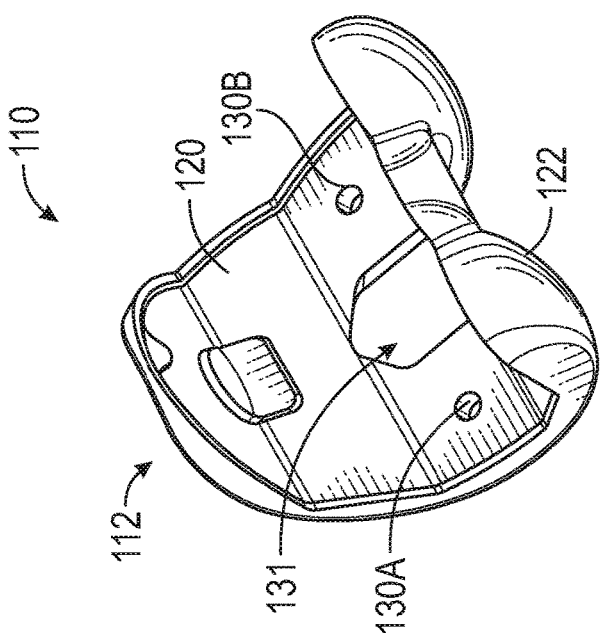
FIG. 2
FIG. 2A

KNEE PROSTHESIS SYSTEM AND METHOD

FIELD

The present subject matter relates to orthopedic procedures and, more particularly, to systems and methods used in knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones of the joint. Cut guides are used to guide the removal of the articular surfaces that are to be replaced. Prostheses are used to replicate the articular surfaces. Knee prostheses can include a femoral prosthesis implanted on the distal end of the femur, which articulates with a tibial bearing component and a tibial component implanted on the proximal end of a tibia. Together these components function to replicate the kinematics of a healthy natural knee. Various types of knee arthroplasty procedures are known including a total knee arthroplasty (TKA), where all of the articulating compartments of the joint are repaired with prosthetic components.

Overview

This disclosure pertains generally to systems for knee arthroplasty and related methods. Clinical needs may necessitate providing various systems of prostheses. For example, during a TKA the physician may encounter unexpected situations such as poor bone quality, soft tissue degeneration or soft tissue/implant mismatch. In some cases, it may be desirable to provide for a more stabilized knee prostheses design, for example, having different, larger and/or more features to facilitate fixation and/or constraint of the knee prosthesis to the patient's bone then was originally anticipated. However, providing additional knee prosthesis systems of different configurations, each having its own separate sub-systems of components and instruments for the TKA (systems and sub-systems which may never be used) can add cost, inventory, and other logistics related complications for both the provider and the manufacturer.

The present inventors have recognized, among other things, improvements to reduce or eliminate the need to rely on large and complex systems and subsystems of components. In particular, the present inventors have disclosed in this document modular systems that can be used to convert a non-stemmed femoral prothesis to stemmed femoral prosthesis to provide for better fixation to the femur. Additionally, the inventors have disclosed modular systems that can be used to convert a non-boxed and/or non-augmented femoral prothesis to a boxed and/or an augmented femoral prosthesis. Such stemmed femoral prostheses, augmented and/or boxed femoral prostheses can meet the clinical need of providing improved fixation of the knee prosthesis to the patient's bone and/or increased joint stabilization should such fixation and/or stabilization be desired.

The present inventors have further recognized, among other things, improvements to increase the compatibility of various components (again to reduce the total parts required for the TKA). Thus, should one desire to modify the femoral prosthesis to add further fixation to the femur; various design types of features to accomplish such modification can be provided and corresponding design types of tibial bearing components (sometimes called tibial bearing prostheses, tibial bearings, bearings, poly or bearing components) are provided to be compatible with the various design types of the features.

For example, if no stem for the assembly including the femoral prosthesis is deemed desirable, the present inventors have designed a base femoral posterior-stabilized (PS) prosthesis, which can couple with one of a PS box (first features) or a mid-level constraint (MLC) box (a second feature). These first and second features do not have a stem, thus, the femoral prosthesis will be stemless.

Alternatively, if a stem for the assembly including the femoral prosthesis is deemed desirable, the base femoral PS prosthesis can couple with a PS box having a stem (a third feature), a MLC box having a stem (a fourth feature) or even a revision box having a stem (a fifth feature). This modular system allows the physician to employ either a PS tibial bearing component or a MLC bearing component as desired. The systems are also contemplated for other types of primary knee design types to improve compatibility such as ultra-congruent (UC) and cruciate-retaining (CR) prostheses, for example. For example, in some instances it may be desirable to utilize a base femoral CR prosthesis that can couple to a stem to provide for additional fixation. The base femoral CR prosthesis may be compatible to be used with a UC tibial bearing component or a CR bearing component as desired. Additionally, the systems disclosed are applicable to instruments such as a trial (sometimes called provisional) that is designed to simulate the size and shape of the femoral prosthesis and/or the tibial bearing component.

In view of the above, the term "femoral prosthesis" or the like as used herein can be any known design type such as a revision, PS, MLC, UC or CR, for example. The term "femoral prosthesis" can further mean a trial component shaped to simulate an implant according to some examples. Similarly, the term "tibial bearing component" or the like can be any known design type such as a revision, PS, MLC, UC or CR, for example. The term "tibial bearing component" can further mean a trial component shaped to simulate an implant according to some examples.

To further illustrate the systems and methods disclosed herein, the following non-limiting examples are provided:

Example 1 is a system for a knee arthroplasty that can optionally comprise: a femoral prosthesis having a joint facing surface and an opposing bone facing surface, wherein the femoral prosthesis has one or more attachment elements at or adjacent the bone facing surface; and one or more features selectively attachable with the femoral prosthesis via the one or more attachment elements, wherein the one or more features comprise one of a box, a stem, or a combination of the box and the stem.

In Example 2, the system of Example 1, wherein the stem can comprise a stem housing configured to attach to a stem extension.

In Example 3, the system of any one or combination of Examples 1-2, wherein the stem can include at least a stem extension.

In Example 4, the system of any one or combination of Examples 1-3, wherein one of the box or the stem can include a bone augment portion configured to overlay with a part of the bone facing surface.

In Example 5, the system of any one or combination of Examples 1-4, wherein the femoral prosthesis can comprise a trial component and the one or more features comprise a plurality of attachments that simulate one or more of the box, the stem or the combination of the box and the stem.

In Example 6, the system of Example 5, wherein at least one of the plurality of attachments can comprise a drill guide.

In Example 7, the system of any one or combination of Examples 1-6, wherein the one or more attachment elements can comprise one of an aperture, a groove, a fastener or a peg.

In Example 8, the system of any one or combination of Examples 1-7, wherein the box comprises a first portion of a segmented box and the first portion can be configured to abut a second portion of the segmented box, the second portion of the segmented box formed by the femoral prosthesis.

In Example 9, the system of any one or combination of Examples 1-8, wherein the one or more features can comprise a plurality of features each having at least one of a different shape or size.

In Example 10, the system of Example 9, wherein the box can comprise at least two boxes each having a different shape.

In Example 11, the system of Example 9, wherein the combination of the box and the stem can comprise at least two combinations of the box and the stem each of the at least two combinations having a different shape relative to one another.

In Example 12, the system of any one or combination of Examples 1-11, can optionally further comprise a plurality of tibial bearing components each having different design type, wherein the femoral prosthesis is configured to articulate through a range of motion with at least a one of the plurality of tibial bearing components without the one of the one or more features attached thereto and at least a second of the plurality of tibial bearing components is configured to articulate through the range of motion with the femoral prosthesis having the one or more features attached thereto.

In Example 13, the system of any one or combination of Examples 1-13, wherein the one or more attachment elements can comprise a peg that is useable with the femoral prosthesis alone or with the femoral prosthesis in combination with the one or more feature attached to the femoral prosthesis.

In Example 14, a system for a knee arthroplasty can optionally comprise: a femoral prosthesis having a joint facing surface and an opposing bone facing surface; a plurality of features each selectively attachable with and removable from the femoral prosthesis at or adjacent the bone facing surface, wherein each of the plurality of features comprise one of a box, a stem, or a combination of the box and the stem; and a plurality of tibial bearing components each having one of a different design type; wherein the femoral prosthesis is configured to articulate through a range of motion with at least a one of the plurality of tibial bearing components without any of the plurality of features attached thereto and at least a second of the plurality of tibial bearing components is configured to articulate through the range of motion with the femoral prosthesis having one of the plurality of features attached thereto.

In Example 15, the system of Example 14, can optionally further comprise one or more pegs configured to attach at least some of the plurality of features to the femoral prosthesis, wherein the one or more pegs are useable with the femoral prosthesis alone without the plurality of features attached to the femoral prosthesis.

In Example 16, the system of any one or combination of Examples 14-15, wherein the box can comprise at least two boxes each having a different shape.

In Example 17, the system of any one or combination of Examples 14-16, wherein the combination of the box and the stem can comprise at least two box and the stem combinations each having a different shape.

In Example 18, the system of any one or combination of Examples 14-17, wherein the femoral prosthesis can comprise a trial component and the plurality of features comprise a plurality of attachments that simulate the box, the stem or the combination of the box and the stem.

In Example 19, the system of Example 18, wherein at least one of the plurality of attachments can comprise a drill guide.

In Example 20, the system of any one or combination of Examples 14-19, wherein the stem comprises a stem housing can be configured to attach to a stem extension.

In Example 21, the system of any one or combination of Examples 14-20, wherein the stem can include at least a stem extension.

In Example 22, a method of determining a desired implant configuration for a knee joint of a patient during a knee arthroplasty comprising: providing a femoral prosthesis mountable to a femur and configured to articulate with at least a first design type of a tibial bearing component, wherein the femoral prosthesis is configured to be modified by attaching one or more features thereto to provide further stabilization to the knee joint; determining if the femoral prosthesis without the one or more features attached would provide adequate one or more of bone fixation of the femoral prosthesis and stabilization of the knee joint; and proceeding to modify the femoral prosthesis by attaching the one or more features thereto if the one or more of the bone fixation and the stabilization of the knee joint is determined to be inadequate.

In Example 23, the method of Example 22, can optionally further comprise changing to a second design type of the tibial bearing component useable with the femoral prosthesis and the one or more features through a range of motion.

In Example 24, the method of any one or combination of Examples 22-23, wherein the femoral prosthesis can comprise a trial component and the one or more of features comprise a plurality of attachments that simulate a box, a stem or a combination of the box and the stem.

In Example 25, the method of any one or combination of Examples 22-24, wherein the one or more features comprise a plurality of features including at least two of a box, a stem, or a combination of the box and the stem.

In Example 26, the systems or methods of any one or any combination of Examples 1-25 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and systems.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 2 is a perspective view of a base femoral prosthesis that can be used as part of a first system in accordance with an example of the present application.

FIG. 2A shows perspective views of modifications made to the base femoral prosthesis of FIG. 2 to create a non-stemmed femoral prosthesis or a stemmed femoral prosthesis with modular features in accordance with an example of the present application.

DETAILED DESCRIPTION

The present application relates to modular systems that include femoral prostheses that have the ability to be selectively modified such as to add or remove a stem, augments or a box to address physician determined needs during a TKA. This application includes a novel way to intraoperatively convert from a non-stemmable to a stemmable femoral prosthesis. This capability can reduce inventory and componentry and provide for a more efficient surgical procedure. The present application also discloses a novel way to intraoperatively increase or decrease tibiofemoral constraint using a single style bearing (same articular surface). This again can reduce inventory and componentry.

In a TKA, both of the medial and lateral condyles of the femur can be resected. Similarly, the tibia can be resected to remove the medial articular surface and the lateral articular surface using a cutting apparatus. Other portions of the knee, e.g., the intercondylar eminence, patella aspects, etc. can also be removed to prepare the knee to accept the TKA prostheses. Depending on the type of TKA, features such as the ligaments can be spared or can also be removed. In a PS TKA, the ligaments such as the posterior cruciate ligament PCL are removed. Prostheses can be implanted on the femur and the tibia and a tibial bearing component can be placed between the femoral prosthesis and the tibial prosthesis to provide for the replaced articular surfaces.

Figure 1:
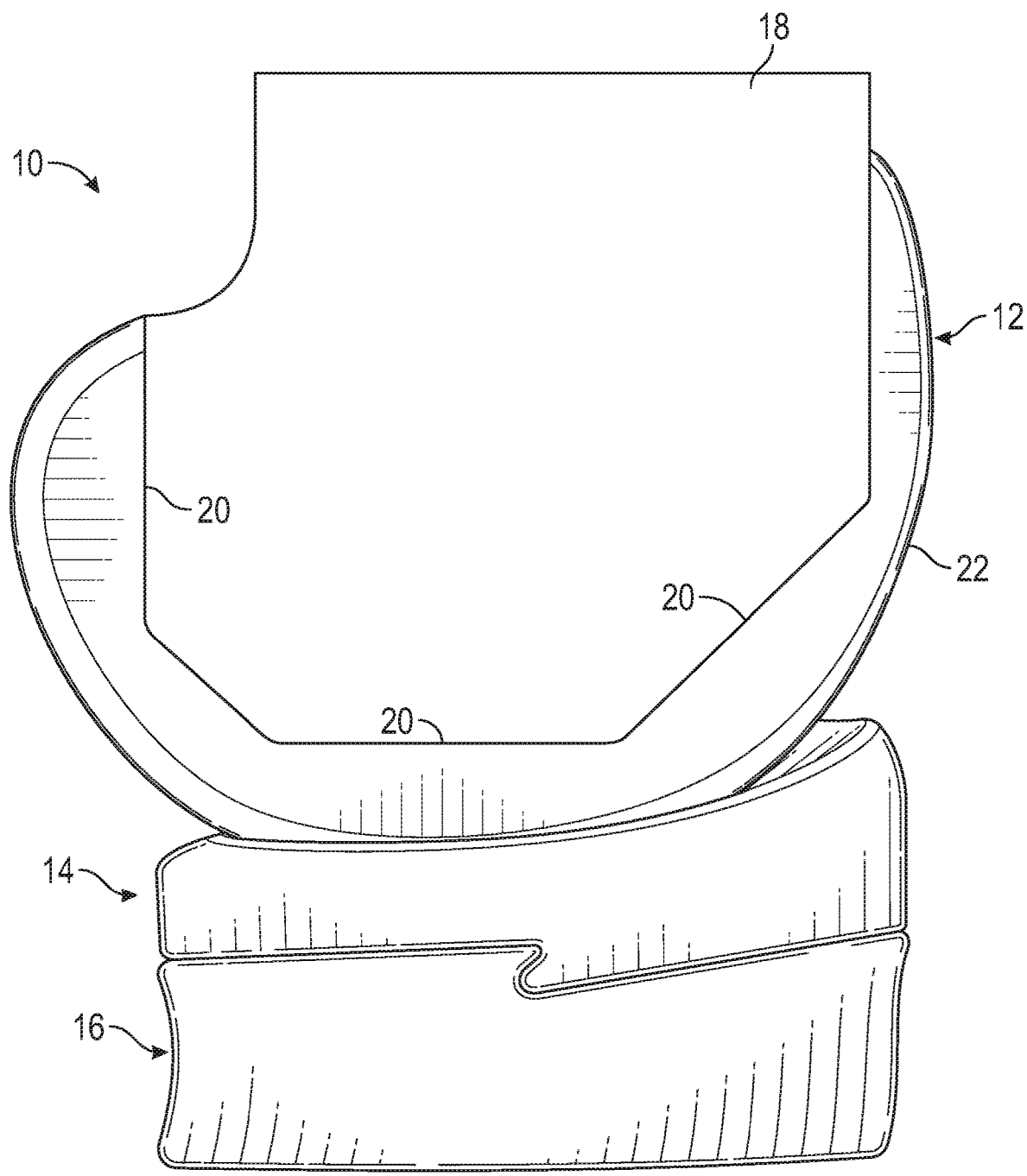
FIG. 1 is a side perspective view of a prosthesis system assembled on a femur, the system including a femoral prosthesis, a tibial bearing component and a tibial prosthesis in accordance with an example of the present application.

FIG. 1 shows a system 10 that includes a femoral prosthesis 12, a tibial bearing component 14 and a tibial prosthesis 16. The system 10 of FIG. 1 represents the arrangement of any of the various systems and components discussed herein. The femoral prosthesis 12 of FIG. 1 is shown implanted on a femur 18. The tibial prosthesis 16 is not shown implanted on a tibia in FIG. 1 but it is understood that in the patient such would be the case.

In FIG. 1, the tibial bearing component 14 is coupled to the tibial prosthesis 16. The femoral prosthesis 12 can be implanted on the femur 18 via a bone interfacing surface 20. The details of the bone interfacing surface 20 will be shown subsequently and can be modified using various features shown and discussed herein. The femoral prosthesis 12 and the tibial bearing component 14 are configured to articulate together through a range of motion of the femoral prosthesis 12 during knee joint flexion and extension. Thus, this range of motion can include both knee joint flexion and extension. The femoral prosthesis can have medial and lateral condyles that can be arcuate in shape having a radius of curvature along an articular surface 22 (also called a joint facing surface herein). The lateral condyle can be configured to be received by a lateral compartment of the tibial bearing component for articulation therewith when the femoral prosthesis 12 is assembled atop the tibial bearing component 14 such as shown in FIG. 1. Similarly, the medial condyle can be arcuate in shape along the articular surface 22 having a radius of curvature. The medial condyle can be configured to be received by a medial compartment of the tibial bearing component for articulation therewith when the femoral prosthesis 12 is assembled atop the tibial bearing component 14 such as shown in FIG. 1.

Further details relating to aspects of the construct of the femoral prosthesis 12 and tibial bearing component 14 can found in U.S. Pat. Nos. 8,858,643, 9,072,607, 8,690,954, 8,764,838, 8,932,365 and United States Application Publication No. 2012/0323336, the disclosures of which are incorporated by reference in their entirety.

According to one example and as will be discussed subsequently, the femoral prosthesis 12 can be designed to be compatible with other commercially available design types of tibial bearing components such as two or more of a revision, PS, MLC, UC or CR, for example. Similarly, according to one example, the tibial bearing component 14 can be designed to be compatible with various commercially available femoral prostheses or types of femoral prostheses as discussed here.

FIG. 1. shows the femoral prosthesis 12 assembled atop the tibial bearing component 14 in full extension (corresponding to 0 degrees flexion). The tibial bearing component 14 is compatible with and configured for operable use to articulate with the femoral prosthesis 12. In particular, the articular surface of the tibial bearing component 14 can be configured to receive the articular surface 22 of the femoral prosthesis 12 thereon and can be configured to allow for articular movement of the femoral prosthesis 12 relative thereto through the range of motion in a manner that simulates the kinematics of a natural knee (e.g., allow for rollback of the femoral prosthesis 12 in flexion including anterior-posterior translation, etc. In some cases, the femoral prosthesis 12 can be configured to facilitate engagement of a spine with a cam (features utilized in a PS or revision type knee system).

The tibial bearing component 14 can comprise a plurality of tibial bearing components as part of the system 10. Each of the plurality of tibial bearing components can have a different design type, for example. The femoral prosthesis can be configured to articulate through a range of motion with one or more of the plurality of tibial bearing components. At least a second of the plurality of tibial bearing components can be configured to articulate through the range of motion with the femoral prosthesis having one of the box, the stem, or the combination of the box and the stem attached thereto as shown in the various systems subsequently.

FIGS. 2 and 2A show a system 110 according to one example of the present application. FIG. 2 shows a base femoral component 112 having a bone interfacing surface 120 configured to interface with a resected femur (not shown in FIG. 2). A joint facing surface 122 (also called an articular surface) of the base femoral component 112 can oppose the bone interfacing surface 120 and can be compatible with one or several types of tibial bearing components (not shown) including one or more of a revision, PS, MLC, UC or CR, for example. According to some examples, the base femoral component 112 can be utilized with certain of the tibial bearing components (e.g., the UC or CR) without features 126 and 128 of FIG. 2A added thereto. It should be recognized that various of the base femoral components further described and illustrated in this application can be compatible with one or more tibial bearing components without modular features attached thereto in the manner of the base femoral component 112 described above.

As shown in FIG. 2, the base femoral component 112 can include one or more attachment elements 130A and 130B configured to facilitate attachment of the features 126 or 128 with the base femoral component 112. The one or more attachment elements 130A and 130B can be located at or adjacent the bone interfacing surface 120. According to the example of FIG. 2, the one or more attachment elements 130A and 130B can comprise threaded apertures that extend from the bone interfacing surface 120 into the base femoral component 112. The one or more attachment elements 130A and 130B can be disposed to either side of an intercondylar recess 131 in the base femoral component 112. Although shown as threaded apertures in FIG. 2, according to other examples (some of which are illustrated subsequently), the one or more attachment elements 130A and 130B can comprise other know mechanical attachment facilitating features (splines, slots, grooves, tabs, projections, fasteners, snap fits, press fits, etc.).

FIG. 2A shows the features 126 and 128 configured to attach with the base femoral prosthesis 112 via the one or more attachment elements 130A and 130B (FIG. 2). Thus, the features 126 and 128 can be configured to attach with the base femoral prosthesis 112 and extend away from the bone interfacing surface 120 when so attached (e.g., extend away generally proximally into the femur (not shown)). In the example of FIG. 2A, the features 126 and 128 can have a plurality of pegs 132A and 132B that can attach the features 126 or 128 to the base femoral prosthesis 112 via threading with the one or more attachment elements 130A and 130B, respectively. The pegs 132A and 132B can provide the system 110 with additional fixation to bone.

The feature 126, if selected, can be attached to the base femoral component 112 and can be configured with a box 134A that inserts into the intercondylar recess 131 in the base femoral component 112. The box 134A can be configured so as to receive and interact with a spine of the tibial bearing component (not shown) during articulation of the knee joint so as to create a PS system, for example. The box 134A can provide further stability to the knee joint through interaction with the spine. The box 134A can additionally project into the bone and can be configured to facilitate cement attachment or bone ingrowth. The pegs 132A and 132B can project into the bone for further fixation thererto. The pegs 132A and 132B can be configured to facilitate bone ingrowth in some examples. Thus, the use of the feature 126 can increase knee joint stability and can increase fixation of the system 110 to bone when compared with use of only the base femoral component 112. However, the feature 126 does not created a stemmed configuration for the system 110 when utilized but does create a PS box configuration, for example.

The feature 128, if selected, can be attached to the base femoral component 112 and can be configured with a box 134B that inserts into the intercondylar recess 131 in the base femoral component 112. The box 134B can be configured so as to received and interact with a spine of the tibial bearing component (not shown) during articulation of the knee joint so as to create the PS system, for example. The box 134B can have the same configuration (e.g., size and shape) as the box 134A. The feature 128 can include a stem housing 135 in addition to the box 134B. In FIG. 2A, the feature 128 creates a stemmed and boxed configuration (e.g., additional fixation to bone above that of the use of the feature 126) for the system 110 when utilized.

According to some examples, the pegs 132A and 132B can be useable with the base femoral prosthesis 112 alone or with the base femoral prosthesis 112 in combination with the one of the box 134A alone, the stem housing 135, or the combination of the box 134B and the stem 135 attached to the base femoral prosthesis 112.

As discussed, in some cases the physician can determine that the base femoral component 112 provides a desired fixation to bone and can be utilized without the features 126 and 128. If the physician determines additional fixation/joint stability is desirable, one of the features 126 or 128 can be selected for use with the base femoral component 112. Feature 128 provides additional fixation to the bone over feature 126 through use of a part or all of the stem 135, 136 (the part sometimes called a stem housing 135 and a remainder of the stem comprising a stem extension 136) is shown in FIG. 2A. The stem extension 136 can be assembled to the stem housing 135 if feature 128 was selected. It should be noted that for the remainder of this application a stem extension is not specifically shown with the various systems. It is understood such stem extension can be part of each of the assemblies. It is further noted that a two-piece stem assembly of a stem extension and stem housing need not be utilized in all examples. Rather, a single piece integral stem or multi-piece stems can be utilized in other examples. Thus, according to some examples only a stem extension and no separate stem housing may be utilized. Additionally, the term "stem" will be used in the present application to designate any one of these multiple possible components or configurations. Thus, the stem housing will simply be referred to as a stem.

Use of the modular system 110 of FIGS. 2 and 2B can eliminate the need for additional dedicated femoral prostheses. One such dedicated femoral prosthesis would be used to create the assembly of the base femoral component 112 with the feature 126 and another dedicated femoral prosthesis would be used to create the assembly of the base femoral component 112 with the feature 128. Thus, inventory, system part number and size and other factors related to the procedure can be reduced.

Figure 3A:
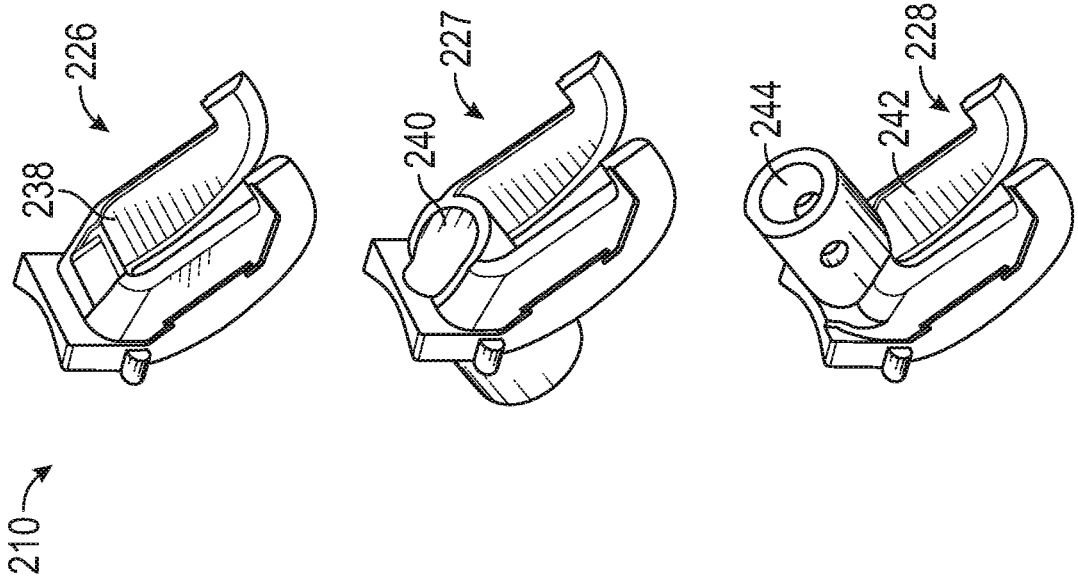
FIG. 3A are perspective views of various modular features that can be mounted to the base femoral prosthesis of FIG. 3 in accordance with an example of the present application.
Figure 3:
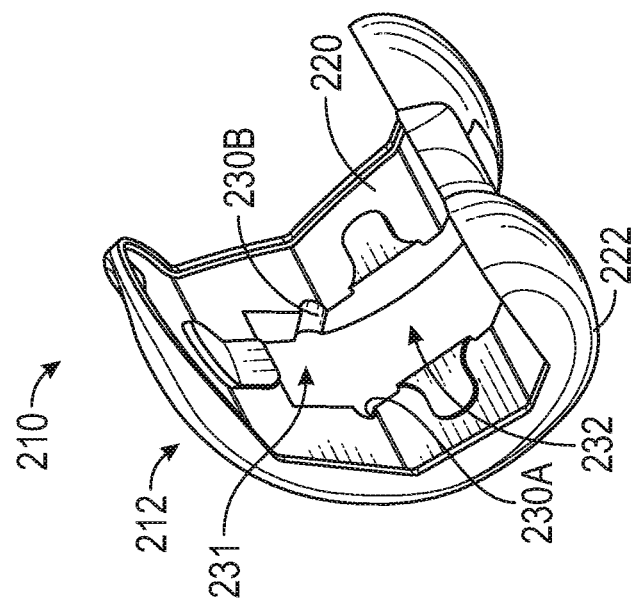
FIG. 3 is a perspective view of yet another example of a base femoral prothesis that can be used as part of a second system in accordance with an example of the present application.

FIGS. 3 and 3A show a system 210 according to one example of the present application. FIG. 3 shows a base femoral component 212 that can comprise a provisional component according to the example of FIGS. 3 and 3A. As such, the base femoral component 212 can be configured to simulate the design of an implant so as to be temporarily inserted into the knee joint to check for appropriate implant size, joint kinematics, etc. FIG. 3 shows the base femoral component 212 having a bone interfacing surface 220 configured to interface with a resected femur (not shown in FIG. 3). A joint facing surface 222 of the base femoral component 212 can oppose the bone interfacing surface 220.

As shown in FIG. 3, the base femoral component 212 can include one or more attachment elements 230A and 230B configured to facilitate attachment of the features 226, 227 or 228 with the base femoral component 212. According to the example of FIG. 3, the one or more attachment elements 230A and 230B can comprise grooves that extend from the bone interfacing surface 220 through the base femoral component 212 to the joint facing surface 222 along a feature receiving portion 231 of the intercondylar recess 232. The one or more attachment elements 230A and 230B can be disposed to either side of the intercondylar recess 232 and can communicate therewith.

As shown in FIG. 3A, the features 226, 227 or 228 can include attachment elements 234A and 234B that are configured to insert in and mate with the one or more attachment elements 230A and 230B. The features 226 and 228 are configured to simulate the geometry of different implant components. The feature 226, when utilized with the base femoral component 212, can comprise a box attachment, and as a provisional component, can simulate a box of an implant. In particular, the feature 226 can include a box feature 238 that is insertable into the feature receiving portion 231 of the intercondylar recess 232.

Feature 227, when utilized with the base femoral component 212, can comprise a drill guide attachment and can be utilized for facilitating drilling into the femur to create an aperture such as to receive a stem of the femoral implant. The feature 227 can have an aperture 240 to facilitate drilling into the femur. Feature 228, when utilized with the base femoral component 212, can comprise a stem and box attachment, and as a provisional component, can simulate a stem and box of an implant. The feature 228 can include a second box feature 242 and a stem feature 244.

Figure 4:
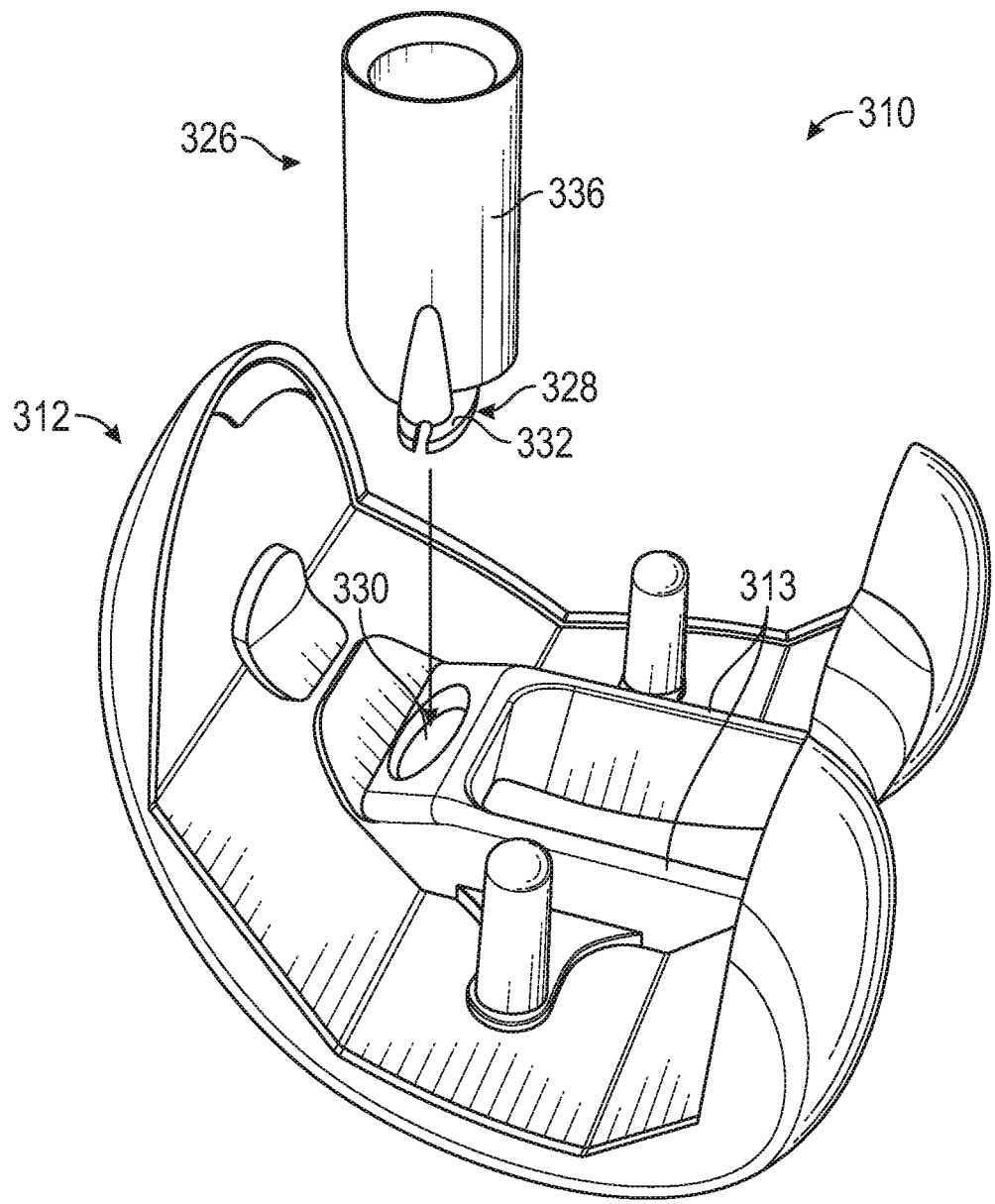
FIG. 4 is a perspective view of another base femoral prosthesis with a stem feature being added thereto as used in a third system in accordance with an example of the present application.
Figure 4A:
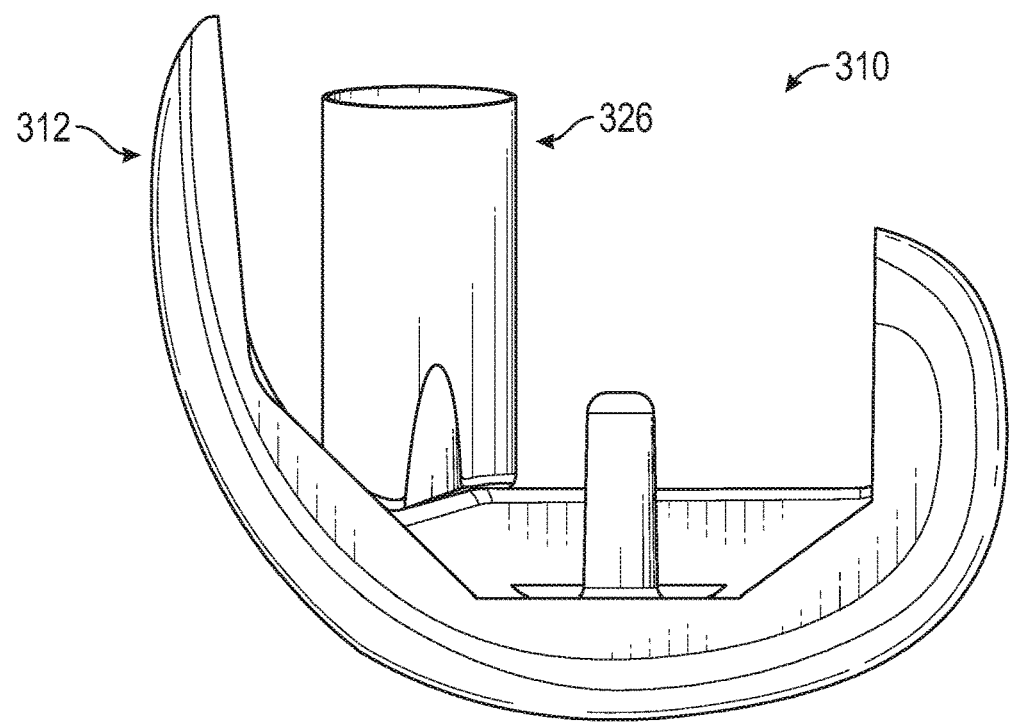
FIG. 4A is a side view of the stem feature of FIG. 4 coupled to the base femoral prosthesis of FIG. 4.

FIGS. 4 and 4A show another system 310 including a base femoral component 312 and a feature 326. The feature 326 can be designed to comprise a stem 336. Unlike prior examples, the base femoral component 312 can include a box 313 as part thereof. The system 310 can be configured to allow for the stem (comprising feature 326) to be added to the base femoral component 312 as desired. The feature 326 can include a proximal aperture configured to receive a remainder of the stem and a distal projection 328 configured to extend into and be received in an attachment element 330 of the base femoral component 312. In particular, the distal projection 328 can include flanges 332 designed to temporarily flex upon insertion into the distal projection 328 and the distal projection 328 includes an overhang features designed to interface and capture the flanges 332.

Figure 5:
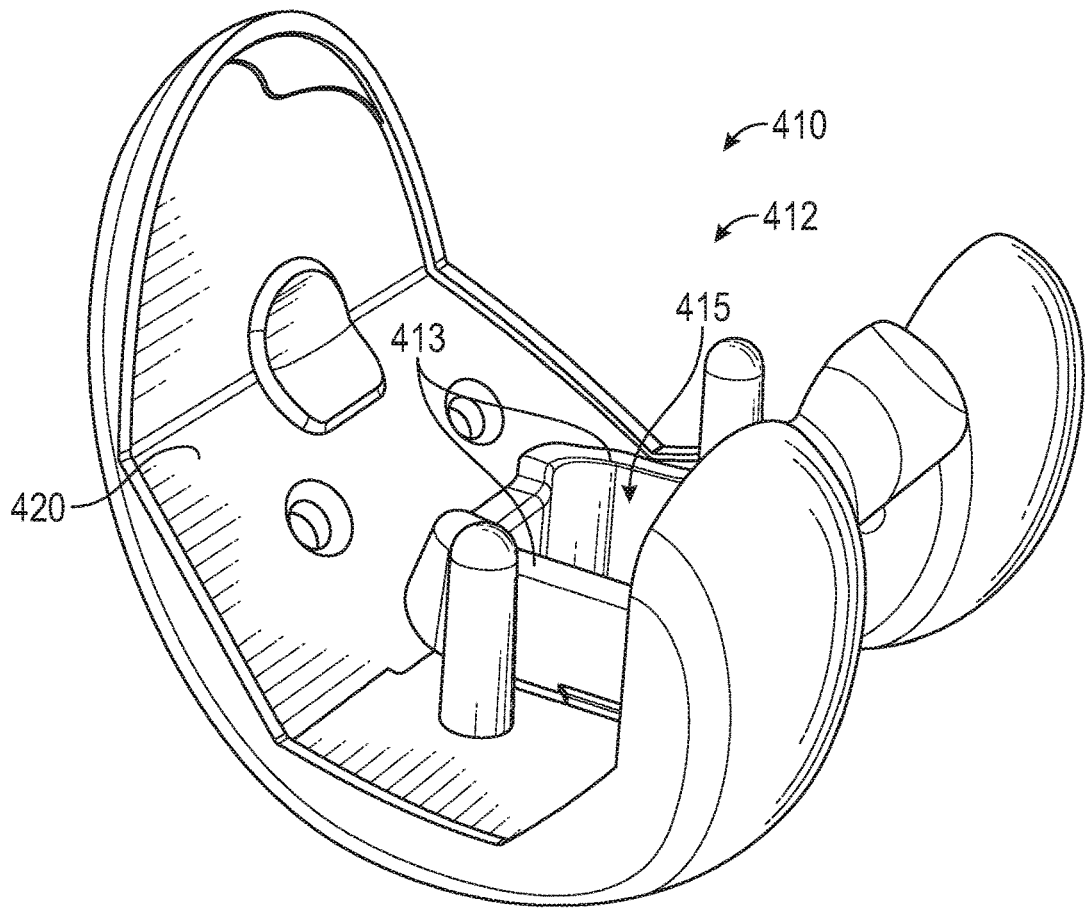
FIG. 5 is a perspective view of yet another base femoral component that can be used as part of a fourth system according to one example of the present application.
Figure 5A:
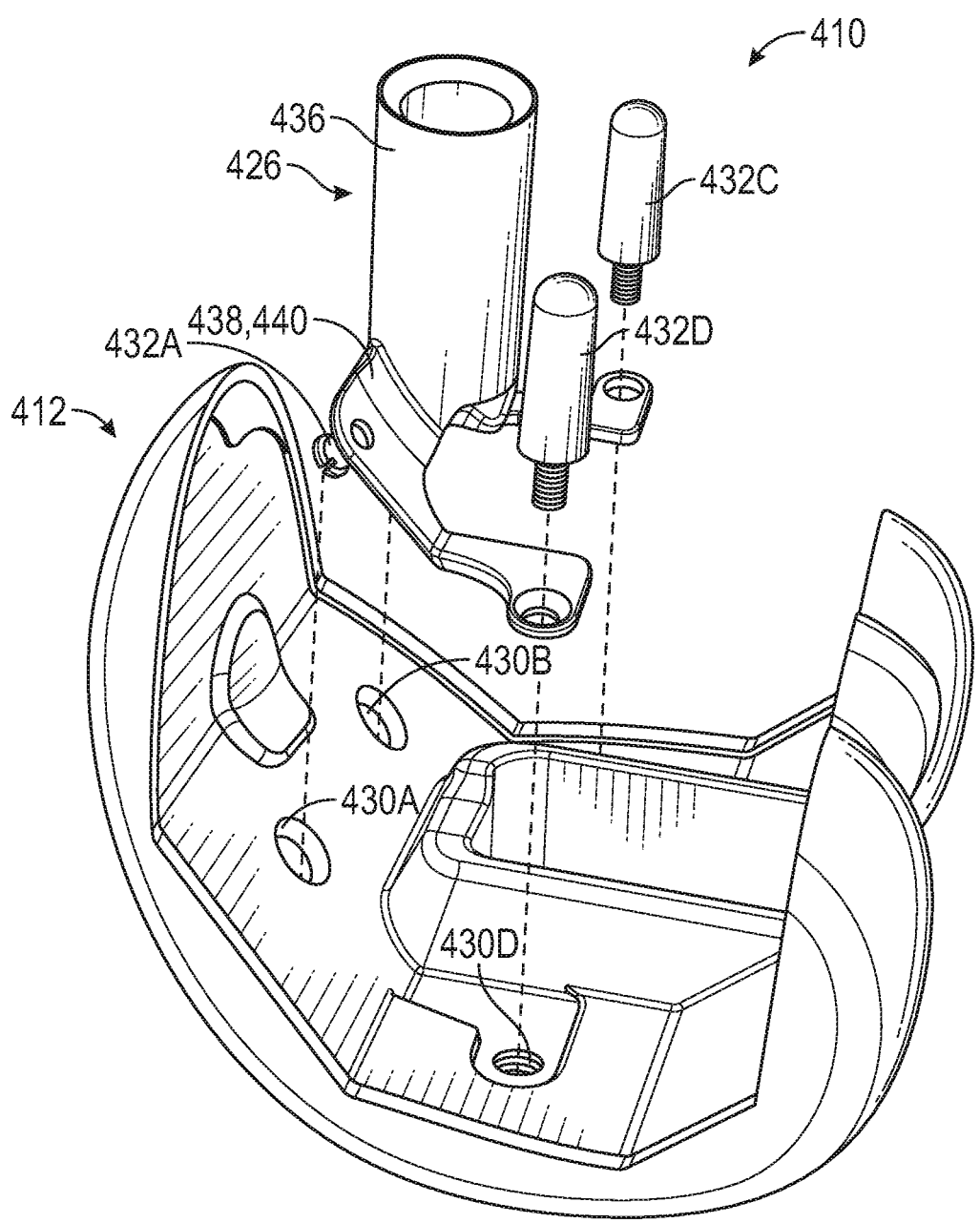
FIG. 5A is a perspective view of the base femoral prosthesis of FIG. 5 with various modular features being added thereto in accordance with an example of the present application.
Figure 5B:
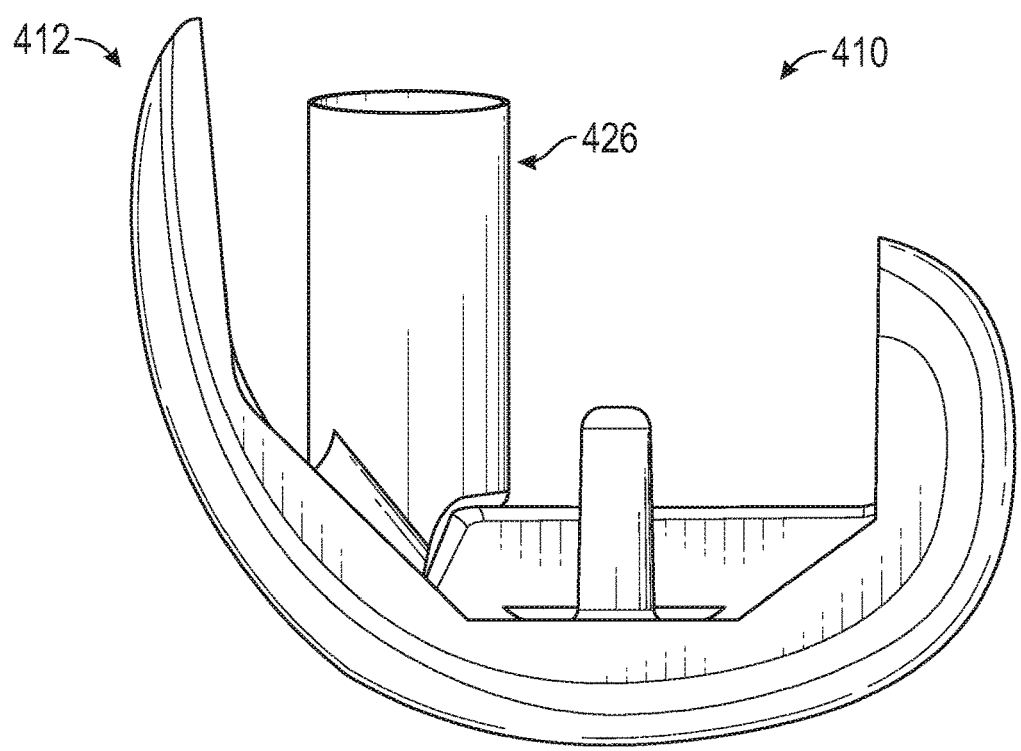
FIG. 5B is a side view of the various modular features of FIG. 5A coupled to the base femoral prosthesis of FIGS. 5 and 5A.

FIGS. 5-5B show another system 410 including a base femoral component 412 and a feature 426 (FIGS. 5A and 5B). FIG. 5 shows the base femoral component 412, which can be configured to be utilized with a tibial bearing component without the feature 426 as with the other examples described herein. The base femoral component 412 includes one or more attachment elements 430A, 430B, 430C and 430D that extend into the bone interfacing surface 420. The base femoral component 412 like that of the example of FIGS. 4 and 4A can include a box 413 as a component thereof as shown in FIG. 5. The box 413 defines an intercondylar recess 415.

FIG. 5A shows the feature 426 being selectively attached to the base femoral component 412. The feature 426 can include attachment elements 432A, 432B (not shown in FIGS.), 432C and 432D configured to correspond to and attach with the one or more attachment elements 430A, 430B, 430C (not shown in FIGS.) and 430D. Via coupling of the attachment elements 432A, 432B, 432C and 432D with the one or more attachment elements 430A, 430B, 430C and 430D, the feature 426 can attach to the base femoral component 412. The attachment elements 432C and 432D can comprise pegs with threaded distal portions as previously described in regard to the example of FIGS. 2 and 2A.

The feature 426 can additionally include a stem 436 and flanges 438 coupled to the stem 436. The flanges 438 can be configured to match a geometry of the bone interfacing surface 420 and can cover over portions of the bone interfacing surface 420 when the feature 426 is attached to the base femoral prosthesis 412. The attachment elements 432A, 432B, 432C (not shown in FIG. 5A) and 432D can couple with a distal surface of the flanges. In some examples, the flanges 438 can be configured as augments 440 that can be configured with porous material to facilitate bone ingrowth into the augment 440 to aid in coupling the system 410 to the femur (not shown).

Figure 6:
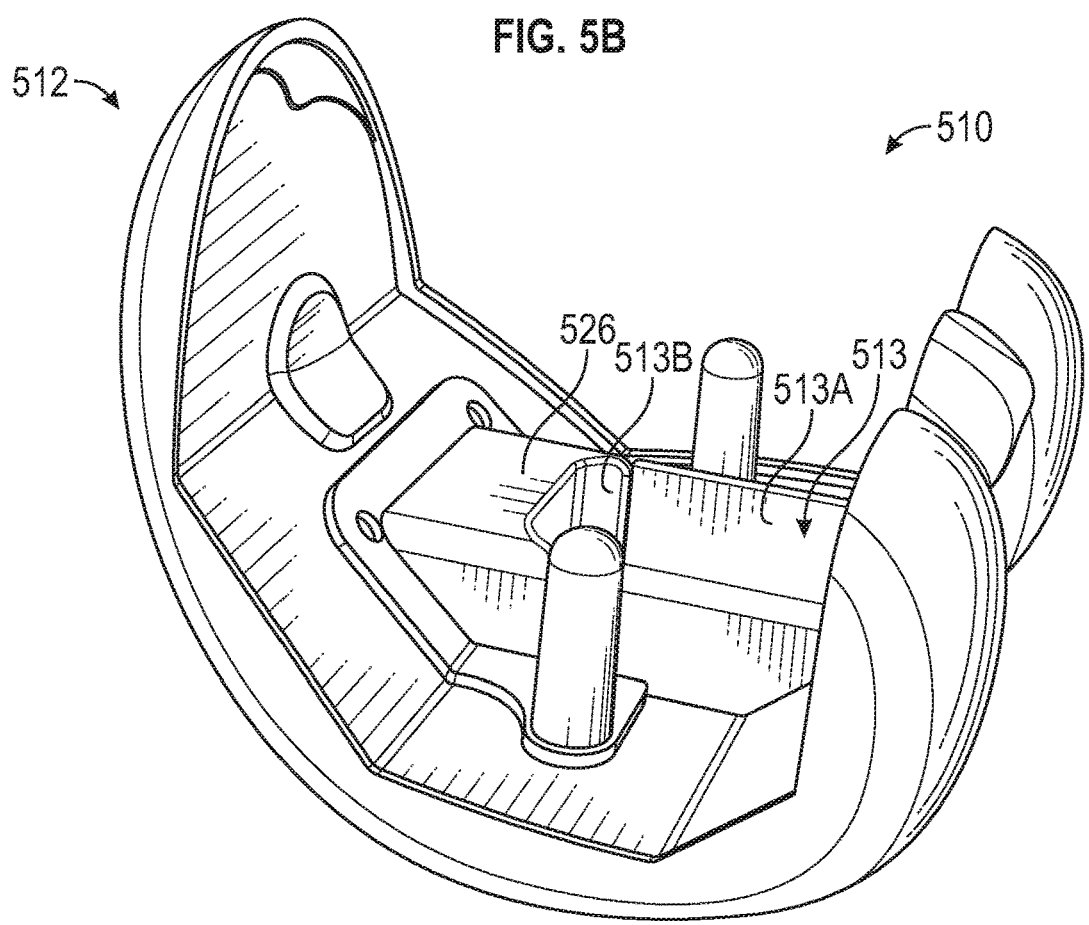
FIG. 6 is a perspective view of yet another base femoral component having a partial box with an additional modular box feature mounted thereto used as part of a sixth system according to one example of the present application.
Figure 6A:
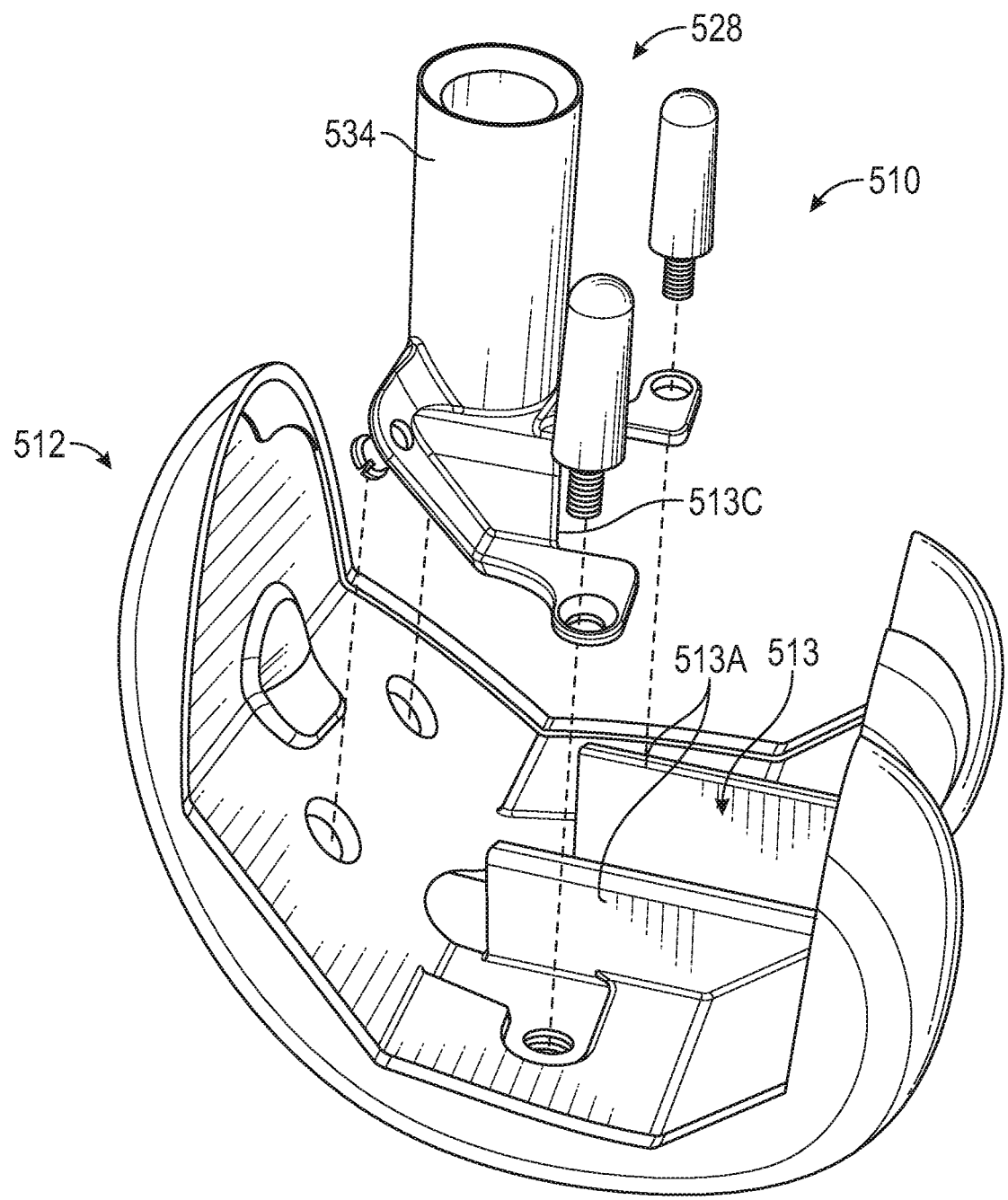
FIG. 6A is a perspective view with the base femoral component of FIG. 6 but with the additional modular box feature removed and stem and box features being added thereto.

FIGS. 6 and 6A show another system 510 of similar construct to that of the system of FIGS. 5-5B, but differing in that a base femoral component 512 and features 526 or 528 can form a part of a box 513. More particularly, as shown in FIG. 6, the system 510 can be attachable with the feature 526 in the manner previously show in FIGS. 5-5B. The base femoral component 512 includes a first portion 513A of the box 513 and the feature 526 includes a second portion 513B of the box 513. Thus, when the feature 526 is attached to the base femoral component 512, together the first portion 513A and the second portion 513B abut to form the box 513.

FIG. 6A shows another feature 528 with a stem 534 being coupled to the base femoral component 512. The feature 528 can be constructed in the manner of the feature 426 but can differ in that it includes a box portion 513C configured to interface with and abut the first portion 513A of the base femoral component 512 when the feature 528 is attached to the base femoral component 512. In this manner, the box portion 513C and the first portion 513A can form the box 513 when the feature 528 is attached to the base femoral component 512.

Figure 7:
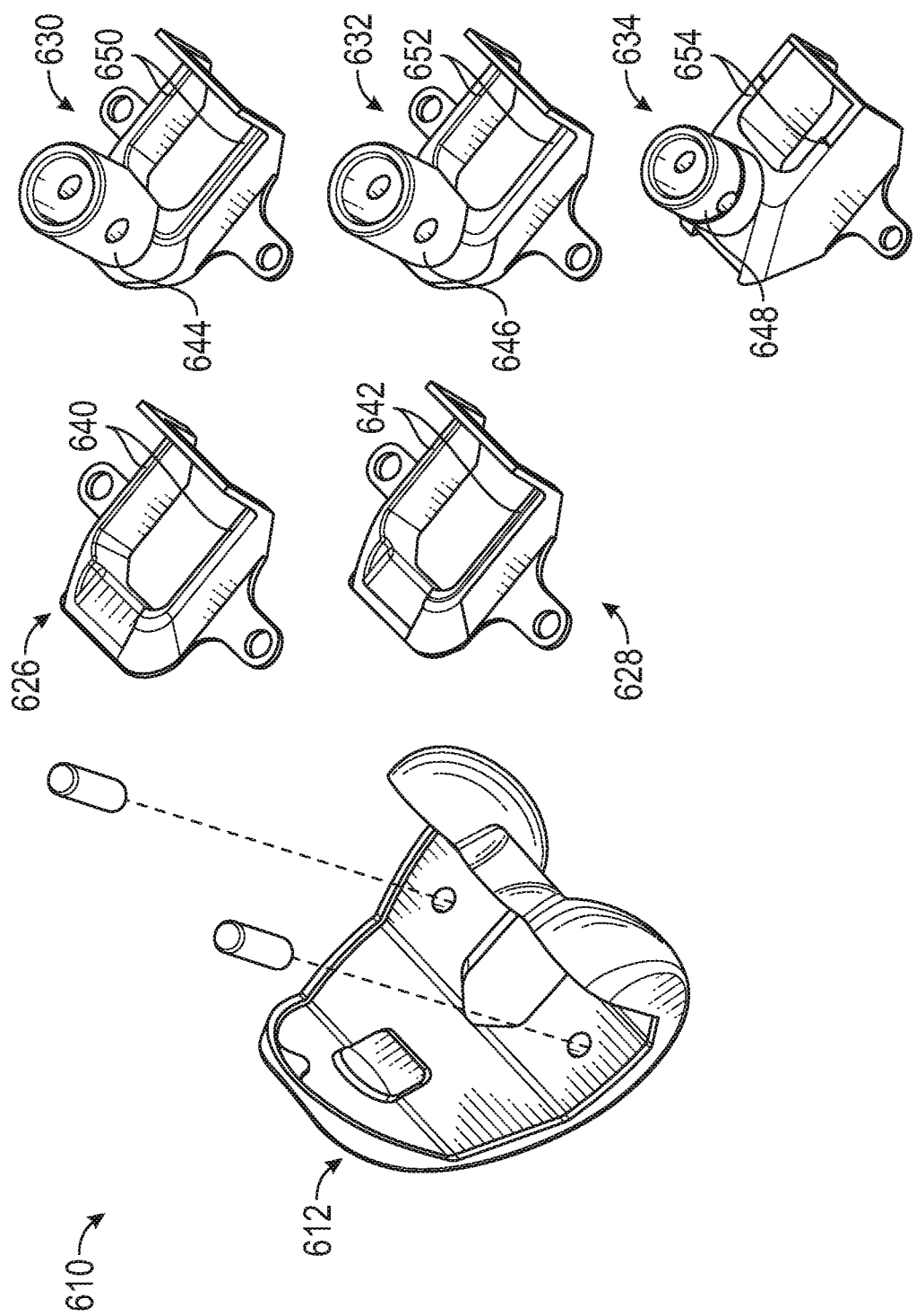
FIG. 7 is a perspective view a seventh system with another base femoral component and a plurality of modular features of different designs in accordance with an example of the present application.

FIG. 7 shows yet another system 610 that can include various features 626, 628, 630, 632 and 634 of differing design (at least one of a different shape or size). The features 626, 628, 630, 632 and 634 can be attachable to a base femoral component 612 with one or more attachment elements 636A and 636B and pegs 638A and 638B as previously illustrated and described. The features 626, 628, 630, 632 and 634 can be configured for use with different types of tibial bearing component configurations. Thus, each of the features 626, 628, 630, 632 and 634 can have a different shape relative to one another. For example, features 626 and 628 can form boxes 640 and 642 of different geometries. The box 640 can be configured for use with a PS tibial bearing component. The box 642 can be configured for use with an MLC tibial bearing component.

The features 630, 632 and 634 can be configured to add stems 644, 646 and 648 to the system 610. However, the feature 630 can have a box 650 that has a different geometry from that of the other features 632 and 634. The box 650 can be configured for use with the PS tibial bearing component, and thus, the box 650 can have a same or similar configuration as the box 640. The feature 632 can have a box 652 configured for use with the MLC tibial bearing component, and thus, the box 652 can have a same or similar configuration as the box 642. The feature 634 can have a box 654 configured for use with a revision tibial bearing component, and thus, differs from both boxes 650 and 652 in configuration.

Figure 8A:
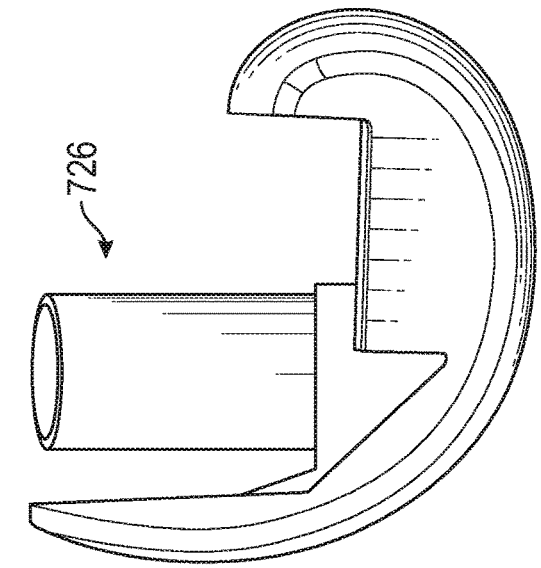
FIG. 8A is a side view of the stem feature of FIG. 8 coupled to the base femoral prosthesis of FIG. 8.
Figure 8:
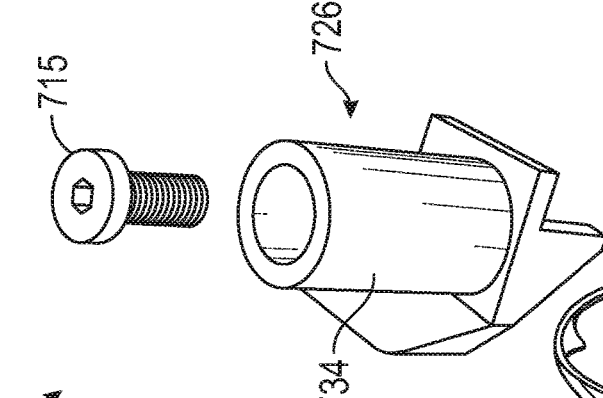
FIG. 8 is a perspective view of an eighth system having yet another base femoral component and a stem feature configured to couple to the base femoral component according to one example of the present application.
Figure 8:
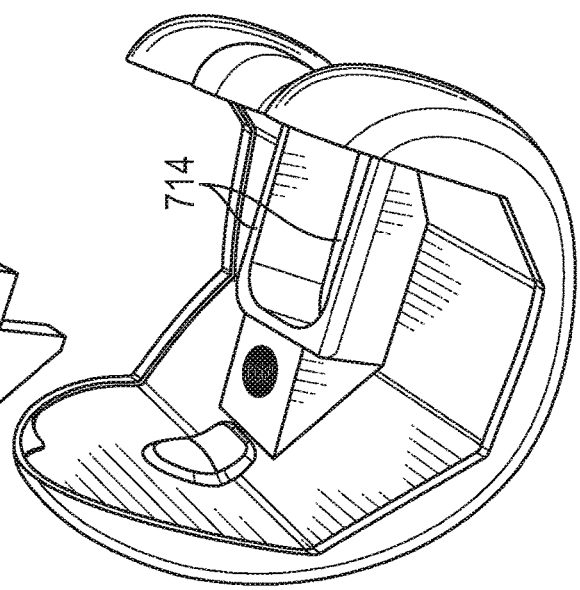

FIGS. 8 and 8A show a system 710 that can include a base femoral component 712 with a box 714 as part thereof. A feature 726 can be added to the base femoral component 712 as desired via a taper bolt 715 that is received in an attachment element 730 (e.g. a threaded aperture as shown in FIG. 7A). The feature 726 can be configured as a stem 732.

Figure 9:
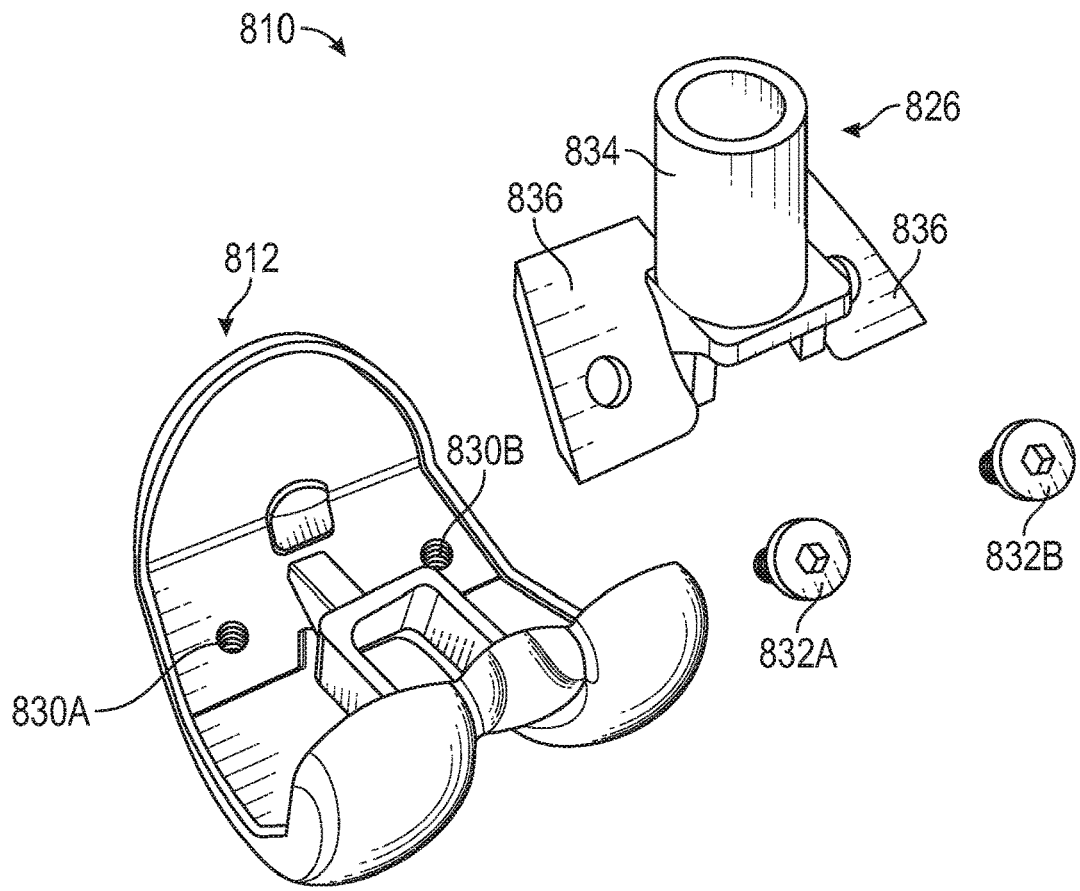
FIG. 9 is a perspective view of a ninth system having a further base femoral component and augment and stem features configured to couple to the base femoral component according to one example of the present application.
Figure 9A:
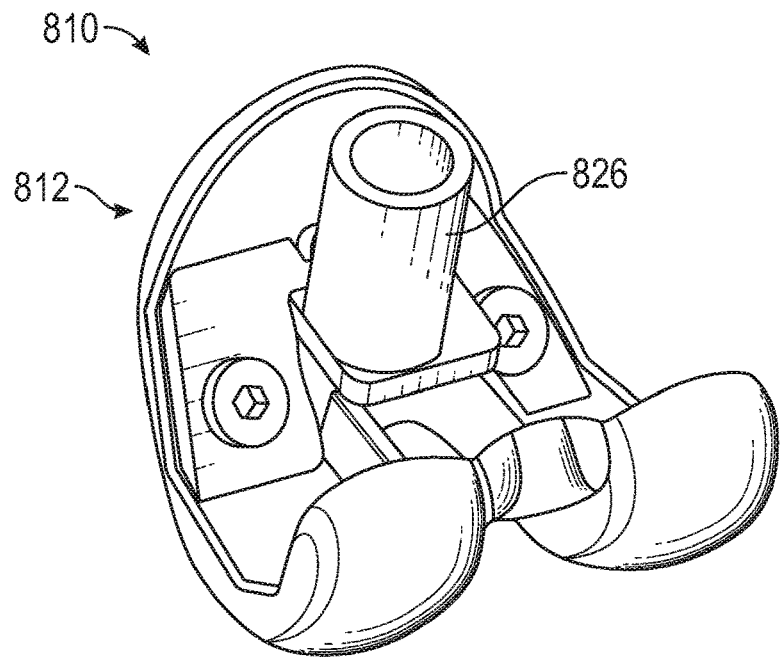
FIG. 9A is a perspective view of the augment and stem feature of FIG. 9 coupled to the base femoral prosthesis of FIG. 9.

FIGS. 9 and 9A show a system 810 with a feature 826 configured to attach to a base femoral component 812. As shown in FIG. 9, the feature 826 can be constructed with a stem 834 and augments 836. The augments 836 can be configured to cover over portions of the bone interfacing surface 820 of the base femoral component 812. The augments 836 can be configured with porous materials to facilitate bone ingrowth to increase fixation of the system 810 with the bone after implantation. Fasteners 832A and 832B can attach the feature 826 to the base femoral component 812 via one or more attachment elements 830A and 830B as shown in FIG. 9.

Figure 10:
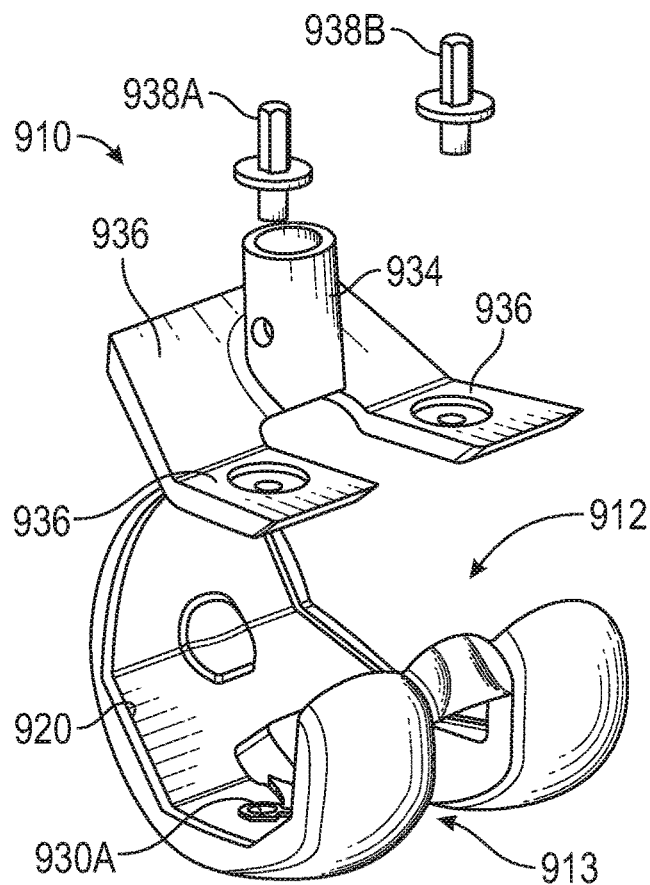
FIG. 10 is a perspective view of a tenth system having another base femoral component and another augment and stem features configured to couple to the base femoral component according to one example of the present application.
Figure 10A:
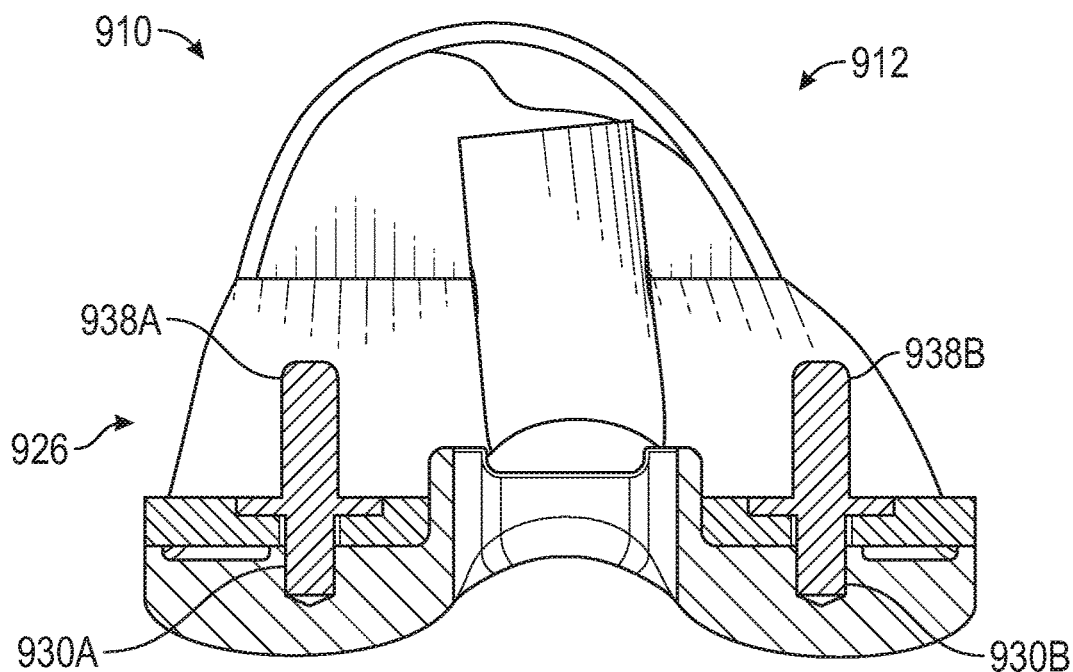
FIG. 10A is a cross-sectional view of the another augment and stem feature of FIG. 10 coupled to the base femoral prosthesis of FIG. 10.

FIGS. 10 and 10A show another system 910 with a base femoral component 912 and a feature 926. As shown in FIG. 10, the base femoral component 912 can include a bone interfacing surface 920 and a box 913. The feature 926 can include a stem 934 and augments 936. The augments 936 can be configured to cover over portions of the bone interfacing surface 920 of the base femoral component 912. The augments 936 can be configured with porous materials to facilitate bone ingrowth to increase fixation of the system 910 with bone after implantation. Pegs 938A and 938B each with threaded distal portions, a flange and peg section can be configured to attach the feature 926 to the base femoral component 912 via one or more attachment elements 930A and 930B (shown in FIG. 10A only).

Figure 11:
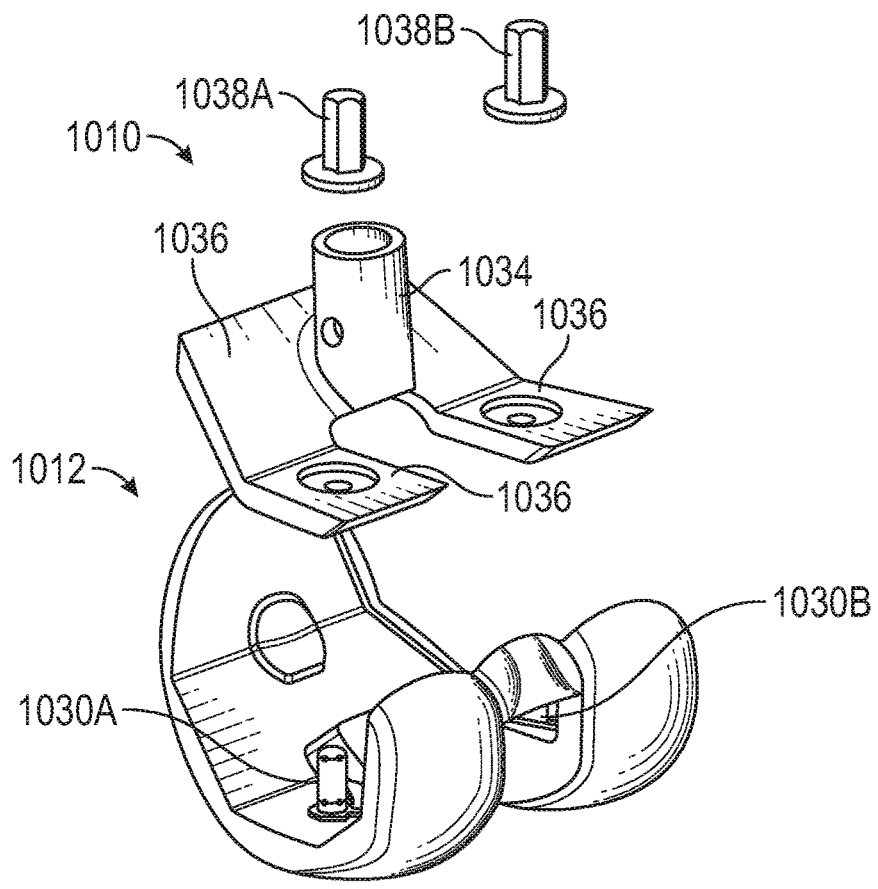
FIG. 11 is a perspective view of an eleventh system having another base femoral component and yet another augment and stem features configured to couple to the base femoral component according to one example of the present application.
Figure 11A:
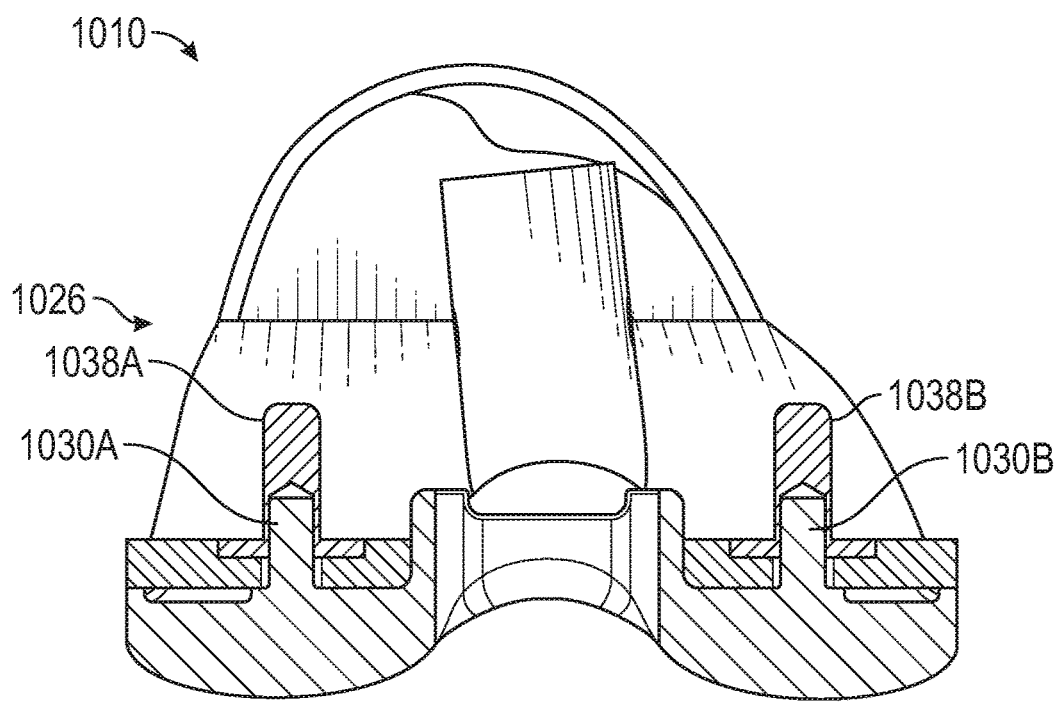
FIG. 11A is a cross-sectional view of the yet another augment and stem feature of FIG. 11 coupled to the base femoral prosthesis of FIG. 11.

FIGS. 11 and 11A show a system 1010 of similar construct to that of FIGS. 10-10A. Thus, the system 1010 includes a base femoral component 1012 and a feature 1026. The feature 1026 can include a stem 1034 and augments 1036 of similar or identical construction to those of the feature 926 of FIGS. 10 and 10A. The base femoral component 1012 differs from that of the base femoral component 912 in that one or more attachment elements 1030A and can comprise projections such as pegs. These can be received by retaining elements 1038A and 1038B. Coupling of the one or more attachment elements 1030A and 1030B with the retaining elements 1038 can attach the feature 1026 to the base femoral component 1012.

Figure 12:
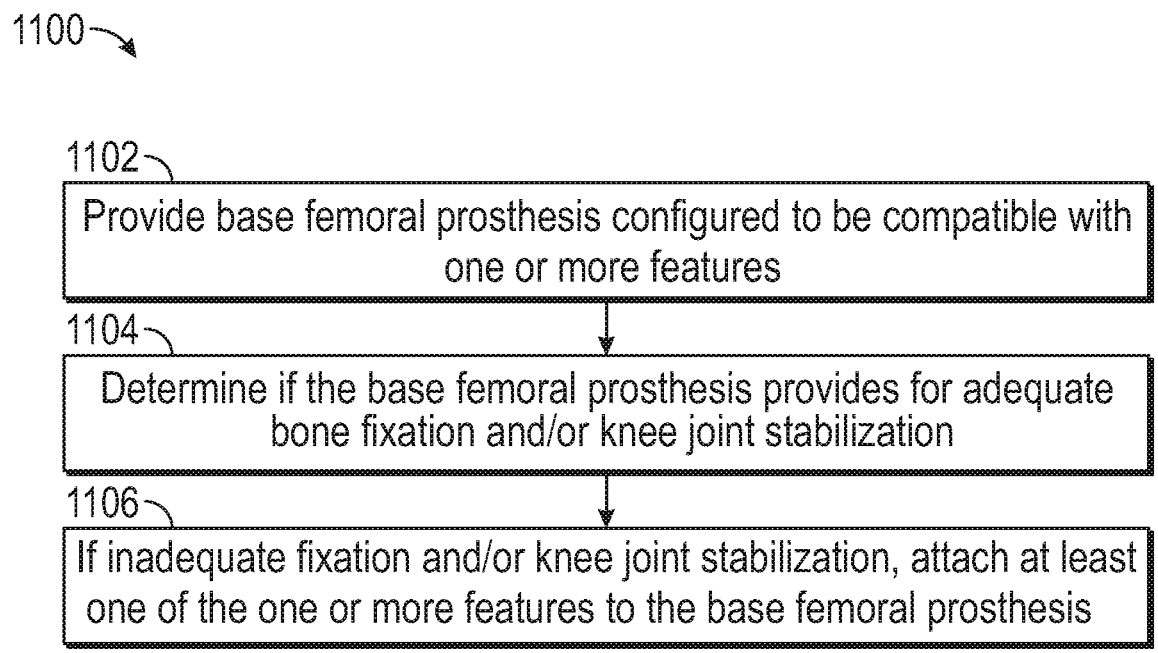
FIG. 12 is a flow chart of a method according to one example of the present application.

FIG. 12 shows a method 1100 of determining a desired implant configuration for a knee joint of a patient during a knee arthroplasty.

The method 1100 can provide at one step 1102 a femoral prosthesis that can be mountable to a femur and can be configured to articulate with at least a first design type of a tibial bearing component. The femoral prosthesis can be configured to be modified by attaching one or more features thereto to provide further stabilization to the knee joint. In another step 1104 of the method 1100, the method can determine if the femoral prosthesis without the one or more features attached would provide one or both of an adequate fixation of the implant and a stabilization of the knee joint. If inadequate stabilization and/or adequate fixation is determined, the method 1100 can proceed to modify the femoral prosthesis by attaching the one or more features thereto at step 1106.

The method 1100 can optionally further include changing to a second design type of the tibial bearing component useable with the femoral prosthesis and the one or more features through a range of motion. The method 1100 can optionally include that the femoral prosthesis comprises a trial component and the one or more of features comprise a plurality of attachments that simulate a box, a stem or a combination of the box and the stem. According to the method 1100 the one or more features can comprise a plurality of features including at least two of a box, a stem, or a combination of the box and the stem.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

As used herein the terms "substantially" or "about" means within two percent of a referenced value, within two degrees of the reference value, within 0.1 mm or less of the reference value, or the like, whatever, context best applies.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for a knee arthroplasty comprising:
a femoral prosthesis having a joint facing surface configured to interface with a tibial bearing component and an opposing bone facing surface having one or more portions thereof configured to directly interface with a femur, wherein the femoral prosthesis has one or more attachment elements at or with openings to the bone facing surface, and wherein the femoral prosthesis has an intercondylar recess therein;
a box configured to be selectively attachable with the femoral prosthesis via the one or more attachment elements;
a stem configured to be selectively attachable with the femoral prosthesis via the one or more attachment elements; and
a combination of the box and stem configured to be selectively attachable with the femoral prosthesis via the one or more attachment elements;
wherein, when selectively attached to the femoral prosthesis, the box and the combination of the box and stem modify a shape of the intercondylar recess; and
wherein the box, the stem and the combination of the box and stem are configured to allow the one or more portions of the bone facing surface to be exposed to directly interface with the femur.

2. The system of claim 1, wherein the stem comprises a stem housing configured to attach to a stem extension.

3. The system of claim 1, wherein the stem includes at least a stem extension.

4. The system of claim 1, wherein one of the box or the stem includes a bone augment portion configured to overlay with a part of the bone facing surface.

5. The system of claim 1, wherein the femoral prosthesis comprises a trial component and the box, the stem and the combination of the box and stem comprise a plurality of attachments that simulate one or more of the box, the stem or the combination of the box and the stem.

6. The system of claim 5, wherein at least one of the plurality of attachments comprises a drill guide.

7. The system of claim 1, wherein the one or more attachment elements comprise one of an aperture, a groove, a fastener or a peg.

8. The system of claim 1, wherein the box comprises a first portion of a segmented box and the first portion is configured to abut a second portion of the segmented box, the second portion of the segmented box formed by the femoral prosthesis.

9. The system of claim 1, wherein the box, the stem and the combination of the box and stem each comprise two or more components having at least one of a different shape or size.

10. The system of claim 9, wherein the box comprises at least two boxes each having a different shape.

11. The system of claim 9, wherein the combination of the box and the stem comprises at least two combinations of the box and the stem each of the at least two combinations having a different shape relative to one another.

12. The system of claim 1, further comprising a plurality of tibial bearing components including the tibial bearing component, wherein each of the plurality of tibial bearing components has a different design type, wherein the femoral prosthesis is configured to articulate through a range of motion with at least a one of the plurality of tibial bearing components without the one of the box, the stem and the combination of the box and stem attached thereto and at least a second of the plurality of tibial bearing components is configured to articulate through the range of motion with the femoral prosthesis having the box, the stem and the combination of the box and stem attached thereto.

13. The system of claim 1, wherein the one or more attachment elements comprise a peg that is useable with the femoral prosthesis alone or with the femoral prosthesis in combination with the box, the stem and the combination of the box and stem attached to the femoral prosthesis.

14. A system for a knee arthroplasty comprising:
a femoral prosthesis having a joint facing surface and an opposing bone facing surface having one or more portions thereof configured to directly interface with a femur, wherein the femoral prosthesis has an intercondylar recess therein;
a plurality of features comprising a box, a stem, and a combination of the box and the stem formed as an integral unit are each selectively attachable with and removable from the femoral prosthesis at or adjacent the bone facing surface, wherein the plurality of features are configured to allow the one or more portions of the bone facing surface to be exposed to directly interface with the femur, and wherein, when selectively attached to the femoral prosthesis, the box and the combination of the box and stem modify a shape of the intercondylar recess; and
a plurality of tibial bearing components each having one of a different design type;
wherein the femoral prosthesis is configured to articulate with at least a first one of the plurality of tibial bearing components without use of any of the plurality of features attached thereto, and wherein the femoral prosthesis is configured to articulate with at least a second one of the plurality of tibial bearing components with one of the plurality of features attached thereto.

15. The system of claim 14, further comprising one or more pegs configured to attach at least some of the plurality of features to the femoral prosthesis, wherein the one or more pegs are useable with the femoral prosthesis alone without the plurality of features attached to the femoral prosthesis.

16. The system of claim 14, wherein the box comprises at least two boxes each having a different shape.

17. The system of claim 14, wherein the combination of the box and the stem formed as the integral unit comprises at least two integral units having box and the stem combinations each having a different shape.

18. The system of claim 14, wherein the femoral prosthesis comprises a trial component and the plurality of features comprise a plurality of attachments that simulate the box, the stem or the combination of the box and the stem.

19. The system of claim 18, wherein at least one of the plurality of attachments comprises a drill guide.

20. The system of claim 14, wherein the stem comprises a stem housing configured to attach to a stem extension.

21. The system of claim 14, wherein the stem includes at least a stem extension.

22. A system for a knee arthroplasty comprising:
a femoral prosthesis having a joint facing surface configured to interface with a tibial bearing component and an opposing bone facing surface having one or more portions thereof configured to directly interface with a femur, wherein the femoral prosthesis has one or more pegs at the bone facing surface, and wherein the femoral prosthesis has an intercondylar recess therein; and
one or more features comprising one of a box, a stem, or a combination of the box and stem are selectively attachable with the femoral prosthesis via the one or more pegs, wherein when selectively attached to the femoral prosthesis the box and the combination of the box and stem modify a shape of the intercondylar recess, and wherein the one or more features are configured to allow the one or more portions of the bone facing surface to be exposed to directly interface with the femur.

* * * * *